US012661097B2

(12) United States Patent (10) Patent No.: US 12,661,097 B2
Zhou et al. (45) Date of Patent: Jun. 23, 2026

(54) DEVICE AND METHOD FOR EXTRACTION OF TISSUE FROM A SUBJECT

(71) Applicants: NICE SURGICAL SOLUTIONS PTE. LTD., Singapore (SG); ALEXANDRA HEALTH PTE. LTD., Singapore (SG)

(72) Inventors: Fangzhou Zhou, Singapore (SG); Zhi Qi Yong, Singapore (SG); Kobby Greenberg, Singapore (SG); Eric Haas, Singapore (SG); Barry Salky, Singapore (SG); Surendra Kumar Mantoo, Singapore (SG)

(73) Assignees: NICE SURGICAL SOLUTIONS PTE. LTD., Singapore (SG); ALEXANDRA HEALTH PTE. LTD., Singapore (SG)

( * ) Notice: Subject to any disclaimer, the term of this patent is extended or adjusted under 35 U.S.C. 154(b) by 136 days.

(21) Appl. No.: 18/565,641

(22) PCT Filed: Jun. 3, 2022

(86) PCT No.: PCT/SG2022/050382
§ 371 (c)(1),
(2) Date: Nov. 30, 2023

(87) PCT Pub. No.: WO2022/255953
PCT Pub. Date: Dec. 8, 2022

(65) Prior Publication Data
US 2024/0252158 A1      Aug. 1, 2024

(30) Foreign Application Priority Data
Jun. 4, 2021    (SG) ........................... 10202106012Y

(51) Int. Cl.
*A61B 17/00*            (2006.01)

(52) U.S. Cl.
CPC ................... *A61B 17/00234* (2013.01); *A61B 2017/00287* (2013.01); *A61B 2217/005* (2013.01)

(58) Field of Classification Search
CPC ........ A61B 17/00234; A61B 17/22032; A61B 17/3423; A61B 2017/00287;
(Continued)

(56) References Cited

U.S. PATENT DOCUMENTS 6,270,505 B1      8/2001   Yoshida et al.
2020/0281627 A1   9/2020   Kim et al.
(Continued)

FOREIGN PATENT DOCUMENTS

WO          2020082052 A1     4/2020

OTHER PUBLICATIONS

International Search Report for Corresponding Application PCT/SG2022/050382 Filed Jun. 2, 2022; Mail Date Jan. 5, 2023.
(Continued)

*Primary Examiner* — Brooke Labranche
(74) *Attorney, Agent, or Firm* — CANTOR COLBURN LLP

(57) ABSTRACT

Disclosed is a device for extraction of a resected tissue or the like from a body comprising an elongate portion having a rounded end; a sleeve assembly comprising an anchor portion for contacting a region around the resected tissue when inflated, and a body portion shaped and dimensioned to receive the resected tissue; the body portion comprises a first end, a second end and a pliable sleeve; the first end and the second end each having a respective diameter greater than a desired diameter of the natural orifice or a tissue opening; wherein the pliable sleeve is disposed between the first end and the second end in a manner which a distance between the first end and the second end is adjustable.

11 Claims, 11 Drawing Sheets

(58) Field of Classification Search
    CPC .... A61B 2017/2215; A61B 2017/3452; A61B
            2017/3486; A61B 2217/005; A61B 10/02
    See application file for complete search history.

(56)                   References Cited

U.S. PATENT DOCUMENTS

2021/0022719 A1      1/2021  Baril et al.
2021/0393259 A1*    12/2021  Haas ................... A61B 17/1114

OTHER PUBLICATIONS

Written Opinion of the International Searching Authority for Cor-
responding Application PCT/SG2022/050382 Filed Jun. 2, 2022;
Mail Date Jan. 5, 2023.

* cited by examiner

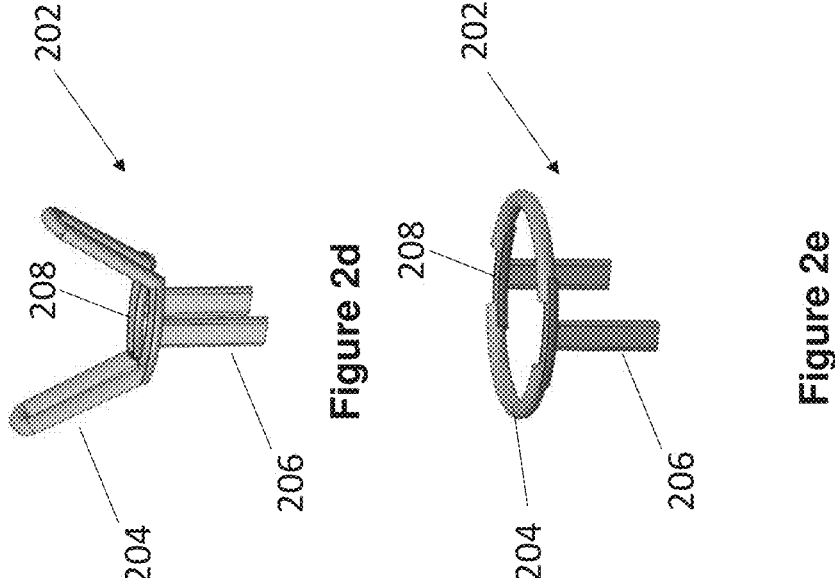
Figure 2d
Figure 2e
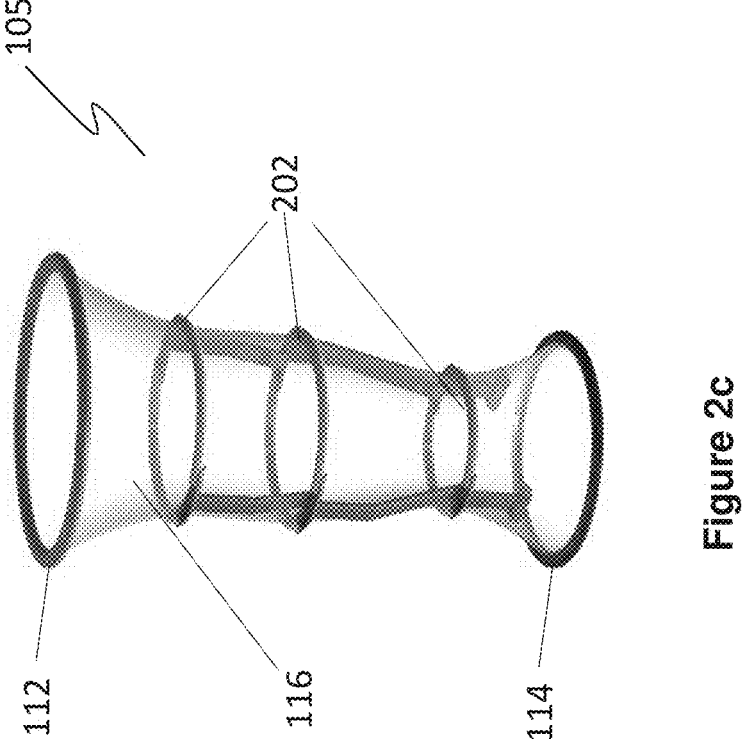
Figure 2c

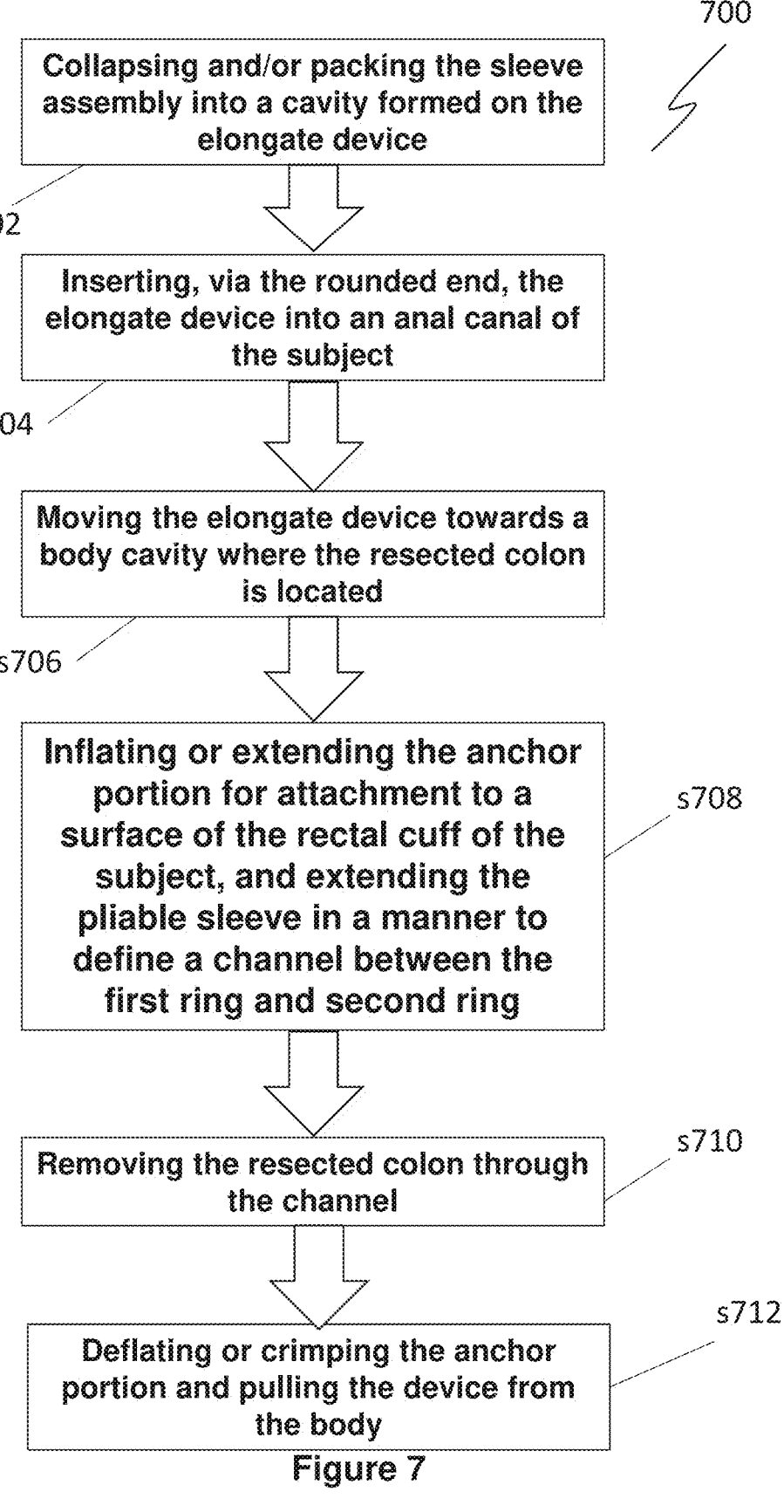

700 s702
Collapsing and/or packing the sleeve assembly into a cavity formed on the elongate device s704
Inserting, via the rounded end, the elongate device into an anal canal of the subject s706
Moving the elongate device towards a body cavity where the resected colon is located s708
Inflating or extending the anchor portion for attachment to a surface of the rectal cuff of the subject, and extending the pliable sleeve in a manner to define a channel between the first ring and second ring s710
Removing the resected colon through the channel s712
Deflating or crimping the anchor portion and pulling the device from the body

Figure 7

DEVICE AND METHOD FOR EXTRACTION OF TISSUE FROM A SUBJECT

TECHNICAL FIELD

The present disclosure relates to a device and a method for extraction of tissue from a subject. The device is particularly suitable for use as a device for the extraction of a resected tissue or the like from a subject, such as a human subject.

BACKGROUND

The following discussion of the background is intended to facilitate an understanding of the present disclosure only. It should be appreciated that the discussion is not an acknowledgement or admission that any of the material referred to was published, known or is part of the common general knowledge of the person skilled in the art in any jurisdiction as of the priority date of the invention.

Surgical or invasive devices have been proposed for the extraction of resected tissue, such as a resected colon. However, such devices face many drawbacks such as difficulty of use and/or inadvertent injury caused to a user when inserted into a body cavity or extracting from the body cavity of the user.

Accordingly, it is an object of the disclosure to provide an improved device and/or method to alleviate one or more drawbacks.

SUMMARY

An aspect of the disclosure is a device for extraction of a resected tissue or the like from a subject comprising an elongate portion having a substantially rounded end; a sleeve assembly comprising an anchor portion for contacting a region around the resected tissue when inflated or extended to a sufficiently rigid state, and a body portion shaped and dimensioned to receive the resected tissue; the body portion comprises a first end, a second end and a pliable sleeve; the first end and the second end each having a respective diameter greater than a desired diameter of the natural orifice or tissue opening; wherein the pliable sleeve is disposed between the first end and the second end in a manner which a distance between the first end and the second end is adjustable.

The device may be a surgical device, and/or may preferably be formed of/from biocompatible materials.

In some embodiments, the elongate portion of the device comprises a cavity adapted to receive the sleeve assembly or part thereof. The elongate portion may comprise a first elongate part and a second elongate part, the first elongate part and the second elongate part joined at an angle. The elongate portion may alternatively be formed of one unified part.

In some embodiments, the elongate portion is formed of or from biocompatible materials such as 316L stainless steel and polypropylene.

In some embodiments, the anchor portion is formed from or of an inflatable or elastic material such as Thermoplastic polyurethane (TPU). In some embodiments the anchor portion is formed from or of a superelastic material such as nickel titanium alloy (nitinol).

In some embodiments, the anchor portion is configured to inflate or expand to a sufficiently rigid ring in a body cavity at a pre-determined temperature.

In some embodiments, the sleeve assembly comprises a dilator disposed at one end of the sleeve assembly and the anchor portion disposed at the other end of the sleeve assembly.

In some embodiments, the dilator is arranged to seal the disposed end of the sleeve assembly.

It is contemplated that the resected tissue may be a resected human colon.

The device may further comprise a spine portion connecting the first end and the second end, the spine portion comprises at least one releasable lever mechanism to move at least one of the first end and the second end between a collapsed state and a non-collapsed state.

The device may further comprise a locking means disposed between the first end and the second end of the pliable sleeve, wherein the locking means is configured to slide in a longitudinal direction of the pliable sleeve.

In some embodiments, the locking means is a crimping mechanism comprising a split ring or crimping member disposed circumferentially around the pliable sleeve, and a support ring disposed along an inner wall of the pliable sleeve, such that the sleeve is sandwiched between the crimping ring and the support ring.

In some embodiments, the crimping ring comprises a lever operable to compress the split ring or crimping member, such that longitudinal movement of the locking means, with respect to the first and second ends, is prevented.

In some embodiments, the support ring has a plurality of bumps disposed along a circumference of the support ring.

According to another aspect of the disclosure there is a method of using the mentioned device to extract a resected specimen, comprising the steps of: a. collapsing and packing the sleeve assembly into a cavity formed on the elongate device; b. inserting, via the substantially rounded end, the elongate device into a natural canal of a mammalian subject; c. moving the elongate device towards a body cavity where the resected specimen is located; d. inflating the anchor portion for attachment to a surface of an inner wall of the body cavity of the mammalian subject, and extending the pliable sleeve in a manner to define a channel between the first end and second end; and e. removing the resected colon through the channel.

The step of removing the resected colon may include inserting a crimping device and pulling the resected colon through the channel. The resected colon may also be removed via other types of devices capable of grasping the resected colon. The crimping device may also be referred to as a grasper.

According to another aspect of the disclosure there is a device for introducing an extractor in a body cavity for removal of a resected tissue, the device comprising an elongate body, a cavity for receiving at least a part of the extractor, and a quick release mechanism for deploying the extractor in the body cavity.

In some embodiments, the extractor has a sleeve assembly comprising an anchor portion for contacting a region around the resected tissue when inflated or extended to a sufficiently rigid state, and a body portion shaped and dimensioned to receive the resected tissue; the body portion comprises a first end, a second end and a pliable sleeve; the first end and the second end each having a respective diameter greater than a desired diameter of the natural orifice or tissue opening; wherein the pliable sleeve is disposed between the first end and the second end in a manner which a distance between the first end and the second end is adjustable.

The resected tissue may be part of a resected colon.

The elongate body comprises a first elongate part and a second elongate part, the first elongate part and the second elongate part may be optionally joined at an angle. In an example, the angle may be a range of any angle above 0 degree to 60 degrees.

According to another aspect of the disclosure there is an extractor device for deployment in a body cavity for removal of a resected tissue comprising a sleeve assembly, the sleeve assembly having an anchor portion for contacting an inner wall of the body cavity when inflated or extended to a sufficiently rigid state, and a body portion shaped and dimensioned to receive the resected tissue; wherein the body portion comprises a first end, a second end and a pliable sleeve, the first end and the second end each having a respective diameter greater than a desired diameter of the natural orifice or tissue opening, and wherein the pliable sleeve is disposed between the first end and the second end in a manner which a distance between the first end and the second end is adjustable.

Other aspects and features of the present invention will become apparent to those of ordinary skill in the art upon review of the following description of specific embodiments of the invention in conjunction with the accompanying figures.

BRIEF DESCRIPTION OF DRAWINGS

In the figures, which illustrate, by way of example only, embodiments of the present invention.

FIGS. 2a to 2j show various embodiments of the extractor as part of the device for extraction of tissue from a subject.

FIG. 7 is a flowchart showing a method of extracting tissue from a subject.

DESCRIPTION OF EMBODIMENTS

As used herein, the term 'subject' includes animals, including mammalian animals and human beings. The term 'subject' includes both living and non-living subjects.

As used herein, the term 'body cavity' refers to cavities or spaces of the body which contain the internal organs, or viscera.

Figure 1B:
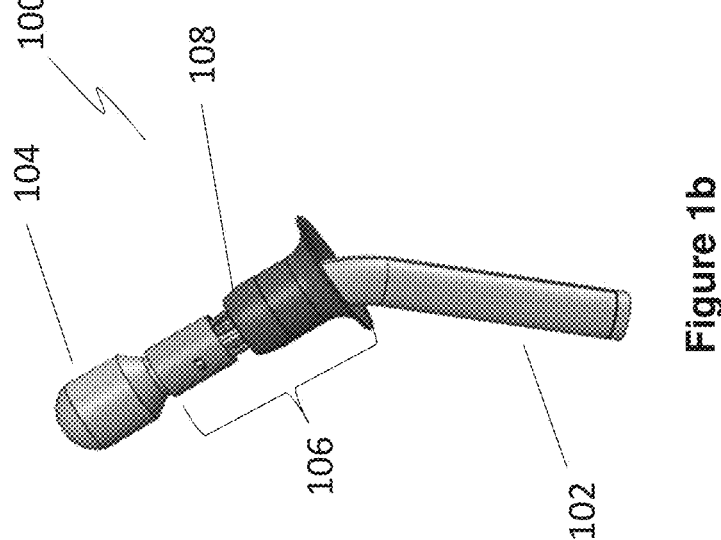
FIG. 1a and FIG. 1b show two embodiments of a device for extraction of tissue from a subject, each device comprising an extractor and an introducer.
Figure 1A:
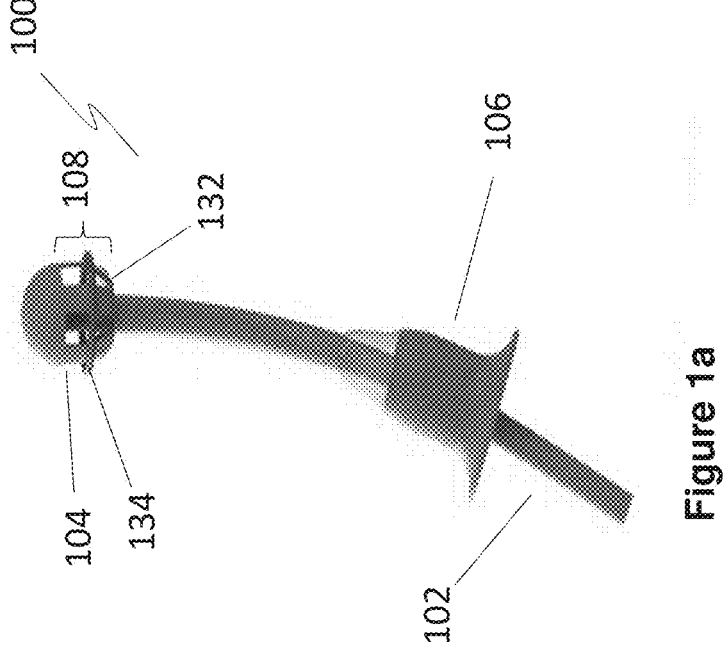

FIG. 1a and FIG. 1b show two embodiments of a device 100 for extraction of a resected tissue, specimen, or the like from a subject. The device 100 may form a surgical device or part thereof. The device 100 is in a pre-deployed form and comprises two parts detachable with respect to each other. The first part may also be referred to as an introducer 101 (refer to FIGS. 3a and 3b), and a second part may be referred to as an extractor 105 (refer to FIGS. 2a to 2f). It is contemplated that the first part and the second part may be manufactured separately and combined before use.

Referring to FIG. 1a, there is shown a device 100 for extraction of a resected tissue or the like from a subject. The introducer 101 comprises an elongate portion 102 having a substantially rounded end 104. The elongate portion 102 may be gently curved so as to facilitate insertion into a body cavity of the subject. The rounded end 104 may be shaped and dimensioned as a ball that has a relatively larger diameter compared to the diameter of elongate portion 102. While the embodiments illustrate the substantially rounded end 104 to be spherical shaped, a skilled person would understand that other shapes may be contemplated, so long as the rounded end 104 is shaped and dimensioned to facilitate insertion into a body cavity of a subject. The rounded end 104 may include a plurality of legs 132 shaped to attach to a part of the sleeve assembly 106 in a pre-deployed state. The pre-deployed state corresponds to a collapsed state of the pliable sleeve 116 shown in FIG. 2a.

The plurality of legs 132 may each comprise hook-like structures at one end of the leg (not shown). The hook-like structure may be attached to a pliable sleeve to minimize inadvertent deployment of the pliable sleeve before it is at the desired location. In addition, a securing means, such as an elastic band 134, may be attached to the plurality of legs 132 to further secure the extractor 105 or part thereof to the elongate portion 102. As an alternative or in addition to the elastic band 134, the plurality of legs 132 may include mechanical structures such as releasable/retractable grips, resilient means such as springs, and/or hooks (not shown) arranged to secure or release the extractor 105. Combinations of the various mechanical structures mentioned may be envisaged. Further, one or more actuators such as push buttons may be arranged with one or more of the aforementioned mechanical structures to effect release of the extractor when the device 100 is inserted into a body cavity.

Referring to FIG. 1b, there is shown another embodiment of the device 100. Unlike the embodiment shown in FIG. 1a, the embodiment of FIG. 1b does not include securing mechanism 132 and elastic band 134 in the vicinity of the rounded end 104. However, the device 100 shown in FIG. 1b includes a slot or cavity 136 (shown in FIG. 3b) for receiving the extractor 105 or part thereof. The slot 136 may include a quick-release mechanism in the form of a locking mechanism 138 for releasing of the extractor 105 when at the desired location within the body cavity. In operation, the quick-release mechanism or locking mechanism 138 is moved (slide) away from the rounded end 104 so as to secure the extractor 105 onto its body. To release, the quick-release mechanism or locking mechanism 138 is pushed or slide towards the rounded end 104 so as to release the extractor 105. This movement of the quick-release mechanism 138 may be facilitated by devices such as levers that are connected to the quick-release mechanism or locking mechanism 138.

The extractor 105 comprises a sleeve assembly 106 having an anchor portion 108. The anchor portion 108 may be inflatable or is an elastic portion for contacting a region around the resected tissue when inflated/extended and a body portion 110 shaped and dimensioned to receive the resected tissue. When deployed within a body cavity as shown in the embodiments shown in FIGS. 2a and 2b, the body portion 110 comprises a first end 112 which forms a contiguous extension from portion 108, a second end 114 and a pliable sleeve 116. The first end 112 and the second end 114 of the body portion 110 each have a respective diameter greater than a desired diameter of the natural orifice or tissue opening; wherein the pliable sleeve 116 is disposed between the first end 112 and the second end 114 in a manner which a distance between the first end 112 and the second end 114 is adjustable.

In some embodiments, the anchor portion 108 may be inflated into a ring for contact/anchor onto a desired body part upon reaching a pre-determined temperature of 24 to 37 degrees Celsius. The anchor portion 108 may be made from any material with sufficient elasticity such that upon being released from compression and/or geometric confinement, the anchor portion resumes substantially its original shape. In some alternative embodiments, the portion 108 is a superelastic material that may be formed from or of a nickel titanium alloy (nitinol), such that it can be flexibly stored in a corresponding introducer and be extended or extended into a ring or a ring-like structure.

Figure 2B:
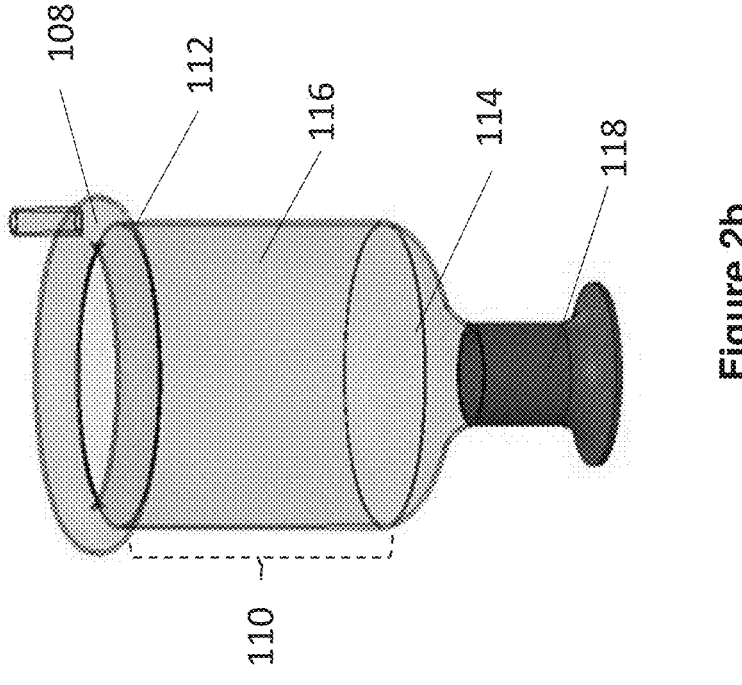
Figure 2A:
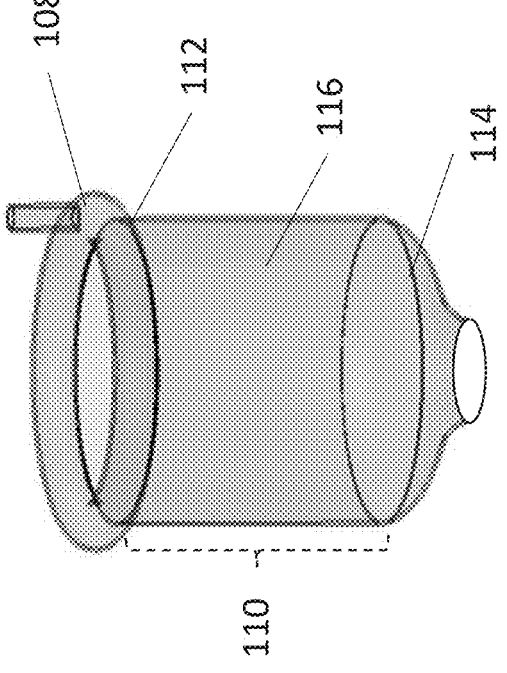

In an embodiment as shown in FIG. 2*b*, the extractor 105 further comprises a dilator 118 disposed at one end of the body portion 110 and the anchor portion 108 disposed at the other end of the body portion 110. The dilator 118 may be an anal dilator such that when the extractor 105 is deployed in the body cavity, an instrument, such as a forceps or the like may be inserted into the body cavity via the anus of the subject to retrieve the resected tissue. The dilator 118 may also be used in other natural canal of the body of a subject.

In another embodiment, the dilator 118 may be replaced with a ring like structure, which is formed of a sufficiently rigid material. The ring like structure functions as anchorage and structural support by providing sufficient tension to the pliable sleeve 116 when deployed in the body cavity of a subject.

The I dilator 118 can be expanded to a maximum diameter and it is appreciable that the dilator cannot be further expanded beyond the maximum diameter. Thus, if an over-sized specimen is pulled through it, the specimen will not be able to go through the dilator 118. Without the dilator 118, the medical practitioner might not be able to deem that the specimen is too big and might still force it through the sphincter muscles, damaging them. Thus, the dilator 118 prevents or minimizes the damage to the sphincter muscles. In some embodiments, the dilator 118 may be formed of or from the same material as the body portion 110, or of a material more rigid than the body portion 110.

FIG. 2*c* shows another embodiment of the sleeve assembly 106 having support structures positioned along the pliable sleeve 116. FIG. 2*c* shows the sleeve assembly 106 in a deployed position which corresponds to the pliable sleeve 116 being extended. Each support structure comprises a ring lever 202. FIG. 2*d* shows a particular ring lever 202 in a collapsed state, and FIG. 2*e* shows the ring structure 202 in an expanded state corresponding to the deployed position shown in FIG. 2*c*. As shown in FIG. 2*c*, multiple ring levers 202 may be positioned between the first end 112 and second end 114 to provide support to the pliable sleeve 116.

Each ring lever 202 comprises two half-rings 204 operable to pivot about a pivot region 208. The two half-rings 204 may be made to pivot about the region 208 via two levers 206. The two levers 206 are connected to the pivot region 208 via a locking mechanism (not shown) in a manner such that when the two levers 206 are moved toward each other, the two half-rings 204 are unlocked and moved away from the plane where the pivot region 208 lies. This may be via a biasing mechanism (not shown)—see FIG. 2*d*. When the two levers 206 are moved away from each other, the two half-rings 204 may be moved to a position coplanar with the plane that pivot region 208 lies—see FIG. 2*e*. When the two half-rings 204 are lying in the same plane as the region 208, they may form a circle. The region 208 may comprise one or more flanges shaped and dimensioned to receive a part of the half-ring 204.

Figures 2F, 2G:
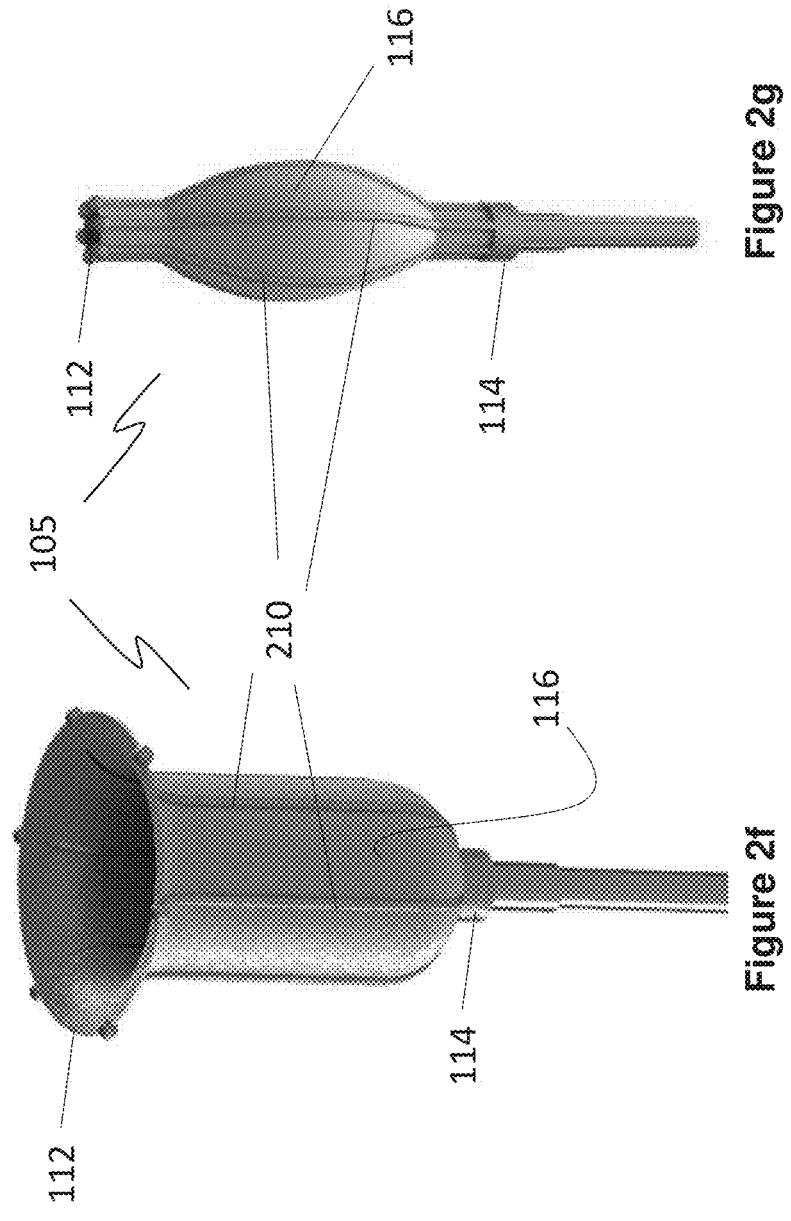

Another embodiment of the extractor 105 is shown in FIG. 2*f* (expanded state) and FIG. 2*g* (collapsed state). The extractor 105 comprises a sleeve assembly 106 having a plurality of spines 210 disposed around a perimeter of the pliable sleeve 116. Each of the plurality of spines 210 may be collapsible so as to enable the sleeve 116 to be pliable. The top portion of the extractor 105 may include a funnel-shaped stent to facilitate the removal of specimen. The funnel-shaped stent may be lined to contain the specimen and minimize and/or prevent tumor seeding. An external sheath (not shown) may accompany the extractor 105 and could be filled with cold fluid (e.g., water/air). The external sheath can be used to crimp or cover the stent after extraction of specimen.

Figures 2H, 2I, 2J:
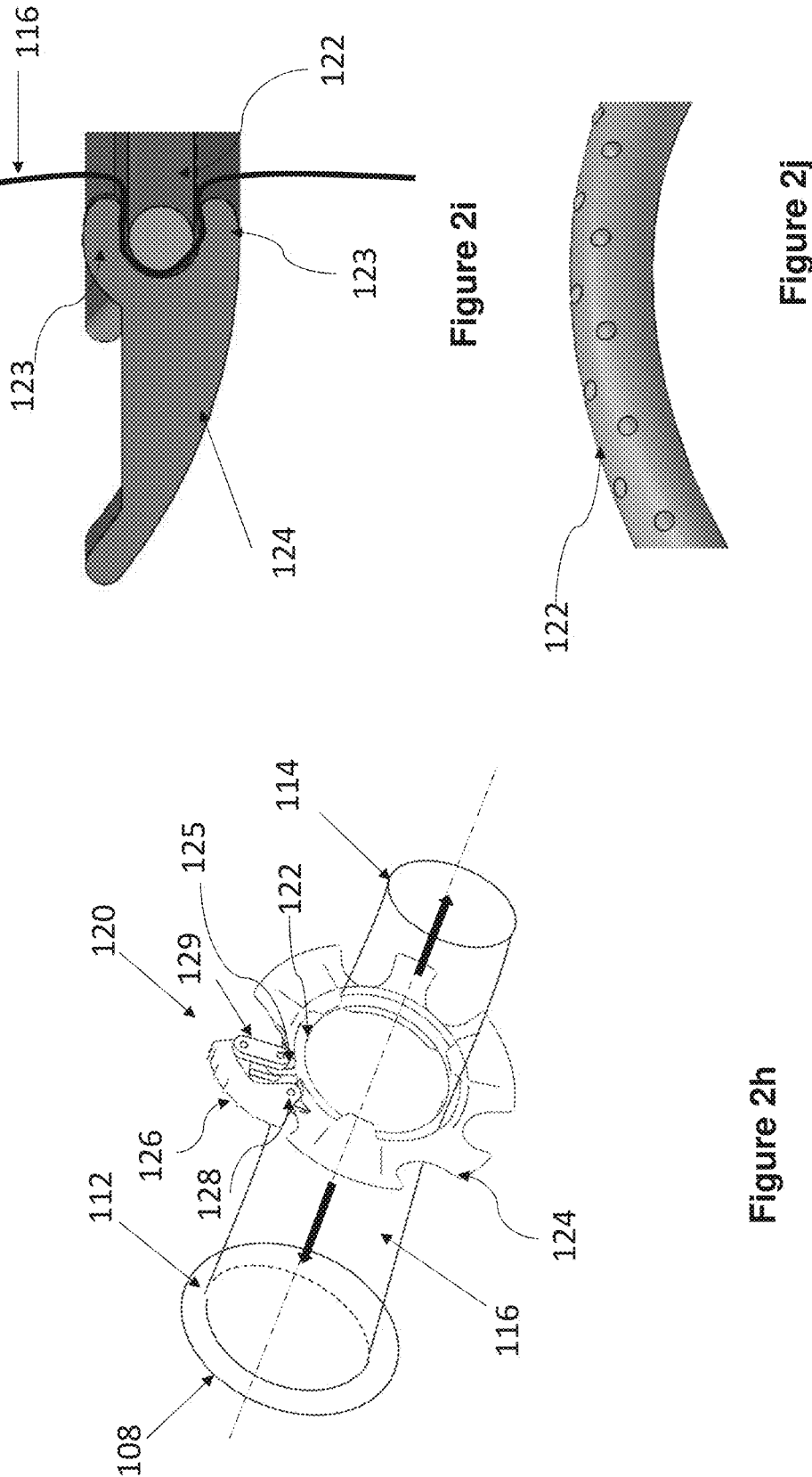

Another embodiment of the extractor 105 is shown in FIG. 2*h*. The extractor 105 comprises an anchor portion 108 for conforming to an inner wall of the body cavity. The pliable sleeve 116 is disposed between the first end 112 and the second end 114. A locking means such as a crimping mechanism 120 is also disposed the two ends 112, 114. In an "open" state, the crimping mechanism 120 is slidable along a longitudinal axis of the pliable sleeve 116 towards the first end 112 or the second end 114. In a "closed" state, the crimping mechanism 120 remains stationery and crimps onto pliable sleeve, thus restricting any movement.

The crimping mechanism 120 comprises a crimping ring 124 which circumferentially surrounds an outer edge of the pliable sleeve 116. The crimping ring 124 may be a split ring formed of 1 or more rings, or a crimping member. A support ring 122 is disposed within an inner edge of the pliable sleeve 116, such that the pliable sleeve 116 circumferentially surrounds the support ring 122, as shown on FIG. 2*i*. The support ring 122 can be a rigid member while the crimping ring 124 may be formed of an elastic material. The crimping ring 124 may be sized and shaped to receive the support ring 122. As shown in FIG. 2*i*, the crimping ring 124 may have a plurality of protrusions 123 which grips on the sleeve 116 and the support ring 122. The crimping ring 124 may also have a C-shaped cross-section. However, the crimping ring 124 may take the form of other shapes and form, so long as it is operable to restrict the longitudinal movement of the support ring 122 with respect to the sleeve, while leaving a closable gap with the support ring 122.

The crimping mechanism 120 may be of any suitable locking or crimping mechanism which may be used to crimp or lock the pliable sleeve 116 against the support ring 122. In the example shown in FIG. 2*h*, the crimping ring 124 has a pivot pin 128 which secures a switch 126, such as a toggle switch, at a first end of the switch 126. The second end of the switch 126 is attached to a pair of levers 129 which is supported by a hinge 125 disposed on the crimping ring 124.

In the "open" state shown in FIG. 2*h*, the switch 126 is in an unlocked position. In this state, the crimping mechanism 120 is free to move in a direction towards the first end 112 or in an opposite direction towards the second end 114, as indicated by the directional arrows in FIG. 2*h*. In the "closed" state, a user will push the switch 126 down towards the clamping ring 124. The switch 126 will thus be locked via the cooperation of the levers 129 and hinge 125. The action of locking the switch 126 will result in the compression of the crimping ring 124 such that the diameter of the crimping ring 124 is now reduced. The reduction in the diameter of the crimping ring 124 causes the gap between the crimping ring 124 and the rigid support ring 122 to be reduced, thus effectively providing a firm and clamping force to clamp the pliable sleeve 116 between the support ring 122 and crimping ring 124. This will prevent the movement of the clamping mechanism 120 towards the first end 112 or second end 114, thus keeping the crimping ring 124 at a desired optimal position to provide tension to the sleeve 116. The support ring 122 may advantageously be provided with a plurality of bumps disposed around the circumference of the support ring 122 (shown in FIG. 2*j*). These bumps serve to provide greater frictional forces between the sleeves 116 and the support ring 122 when in the "closed" state. While the embodiments shown in the figures illustrate the usage of bumps, it may be contemplated that other textures that may similarly provide frictional forces between the sleeve and the support ring, may be used in place of the bumps.

As explained above, the crimping mechanism 120 is not limited to the crimping ring and the locking feature formed by the linkage mechanism shown in the embodiment. Other suitable lock and clamp functions may be applied to the crimping mechanism 120, so long as it is able to close the gap between the support member 122 and the crimping ring 124. For example, the crimping mechanism 120 may be a releasable ratchet lock or a horse-clamp. The adjustable crimping ring improves the usage of the device as it advantageously allows patients of different body sizes to use the device. With the simple release of the lock and slidability of the crimping ring, a user can easily adjust and set the desired length accordingly. Moreover, with such an adjustable sleeve, the manufacturing process is made much easier as the sleeve does not have to be attached (usually by ultrasonic welding) to an additional member. A user operating the extractor will also enjoy greater anchorage from outside of the body of a subject as the effective sleeve length can be adjustable.

Figures 3A, 3B:
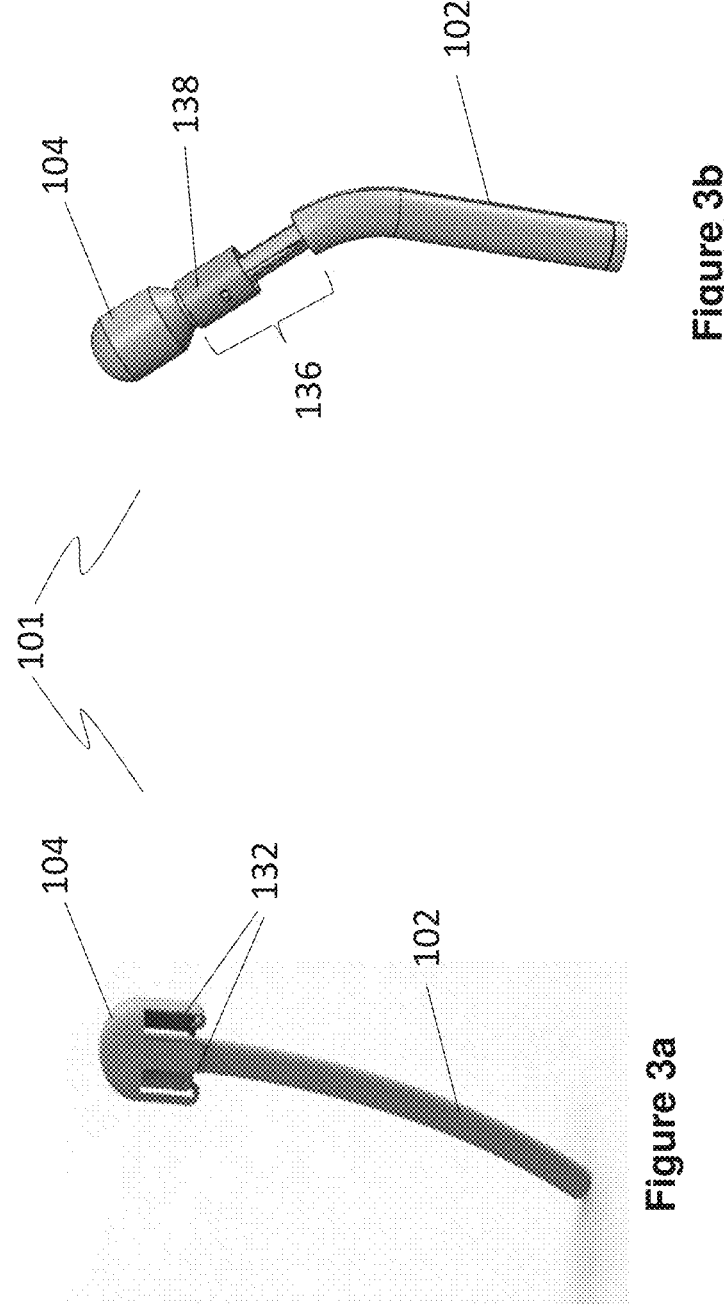
FIGS. 3a and 3b show various embodiments of the introducer as part of the device for extraction of tissue from a subject.

FIGS. 3*a* and 3*b* show embodiments of the introducer 101 of the device 100 without the extractor 105. FIG. 3*a* shows the introducer 101 for use with the embodiment shown in FIG. 1*a*. FIG. 3*b* shows the introducer 101 for use with the embodiment shown in FIG. 1*b*. As may be appreciated, the elastic band 134 (shown in FIG. 1*a* but not in FIG. 3*a*) may be regarded as a quick release mechanism. When the elastic band 134 is attached onto the plurality of legs 132, the legs in turn urge upon the extractor 105 (when present).

Figures 4A, 4B:
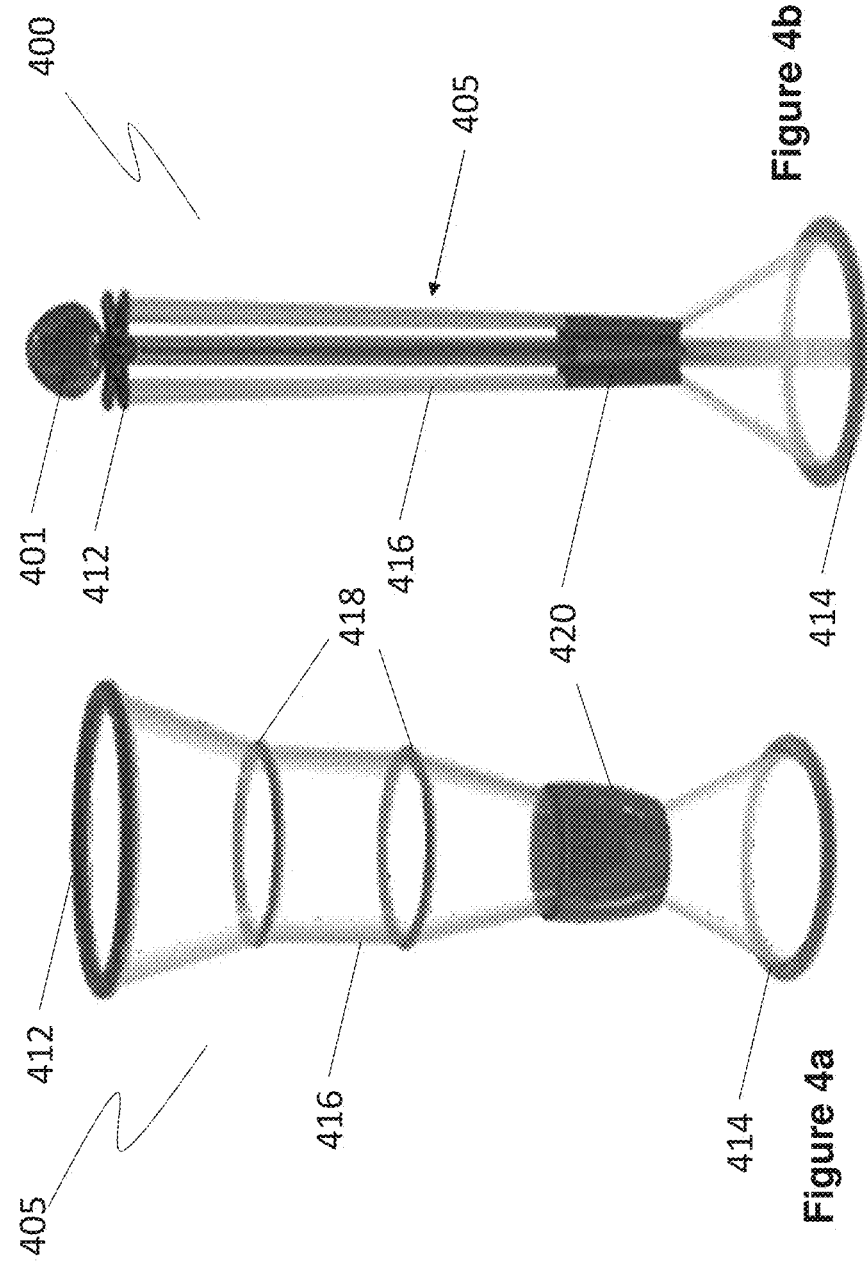
FIGS. 4a to 4c show another embodiment of the device for extraction of tissue from a subject.
Figure 4C:
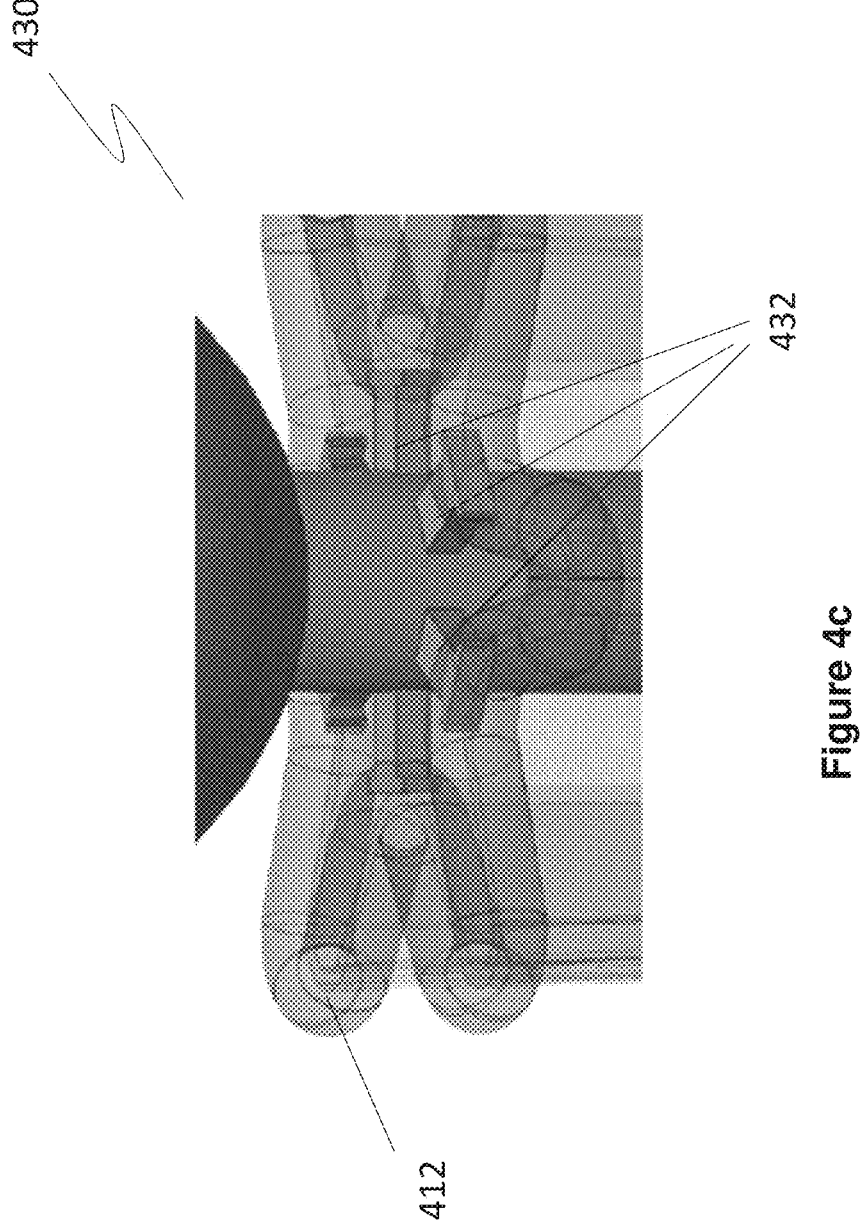

FIGS. 4*a* to 4*c* show another embodiment of a device 400 for extraction of tissue from a subject. FIG. 4*a* illustrates an extractor device 405 in an expanded or deployed state (without an introducer 401). FIG. 4*b* shows the device in a crimped state, attached to the introducer 401. FIG. 4*c* shows a locking mechanism 430 on the introducer 401 which holds the extractor 405 during deployment of the extractor 405 within the body cavity of a subject.

The extractor 405 comprises a flexible ring 412 at one end and a relatively more rigid (but still elastic or compliant) ring 414 at the other end. The rings 412, 414 are connected to each other by a flexible sleeve 416 that has a cylindrical shape or a partially cylindrical shape. Disposed between the rings 412, 414 may be a plurality of rings 418 in its body which help prop open the sleeve 416 to ease removal of bulky specimen. The device 400 may also include one or more semi-rigid component 420 which would be inserted into the body cavity, e.g. an anal canal to straighten it out and minimize or prevent overexpansion of the sphincter muscles. The device 400 comes with an introducer 401 (see FIG. 4*b*) which could engage and disengage the device prior to deployment and during deployment respectively.

The locking mechanism 430 shown in FIG. 4*c* may be in the form of one or more protruding flanges 432 for contracting or receiving corresponding parts of the flexible ring 412 when the flexible ring is folded. In some embodiments, the flexible ring 412 comprises grooves such that when collapsed, each groove is secured to one of the protruding flanges 432.

Figures 5A, 5B, 5C:
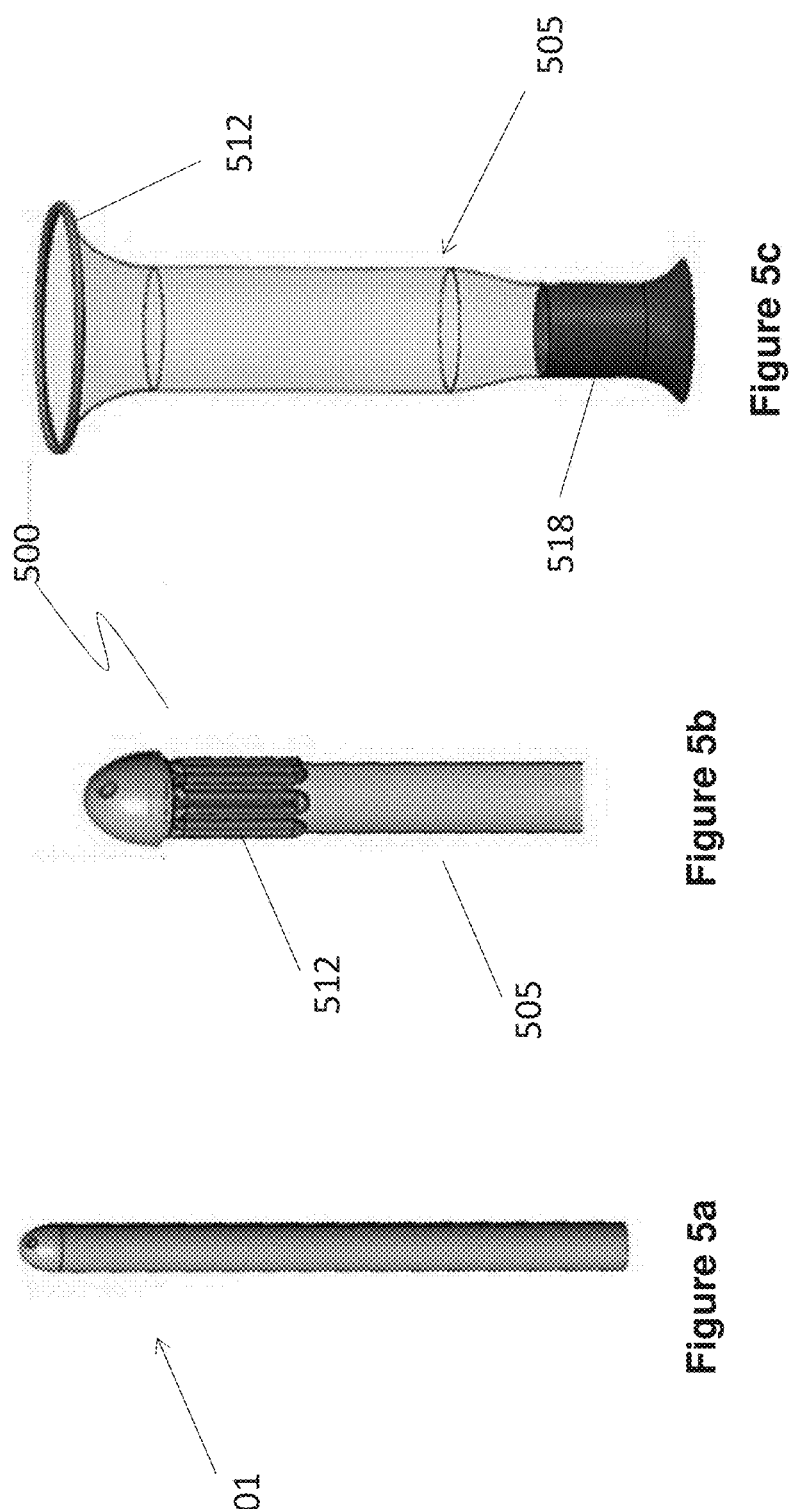
FIGS. 5a to 5c show another embodiment of the device for extraction of tissue from a subject.

FIGS. 5*a* to 5*c* show another embodiment of a device 500 for extraction of tissue from a subject. FIG. 5*a* shows an introducer 501 of the device 500. FIG. 5*b* shows the device 500 in a pre-deployed state, wherein the extractor 505 is folded and secured within a slot of the introducer 501. FIG. 5*c* shows the extractor 505 in a deployed state. The device 500 comprises an elastic top ring 512 which could be folded onto the extractor 505 prior to deployment. Upon reaching the desired body cavity for the extraction of a resected tissue, e.g. a colon, the top ring 512 expands (by virtue of heat) into a ring and anchors onto the edge of the organ, such as colon tissue. It has a cylindrical body whose interior is lubricated to allow the resected specimen to slide out of the natural canal such as the rectum and anal canal. It may also include a dilator 518 that opens the canal of the body while preventing over-expansion of the canal which could damage the sphincter muscles. The introducer 501 has a smooth conical head that allows ease of penetration and functions as an anal sizer.

Figures 6A, 6B, 6C:
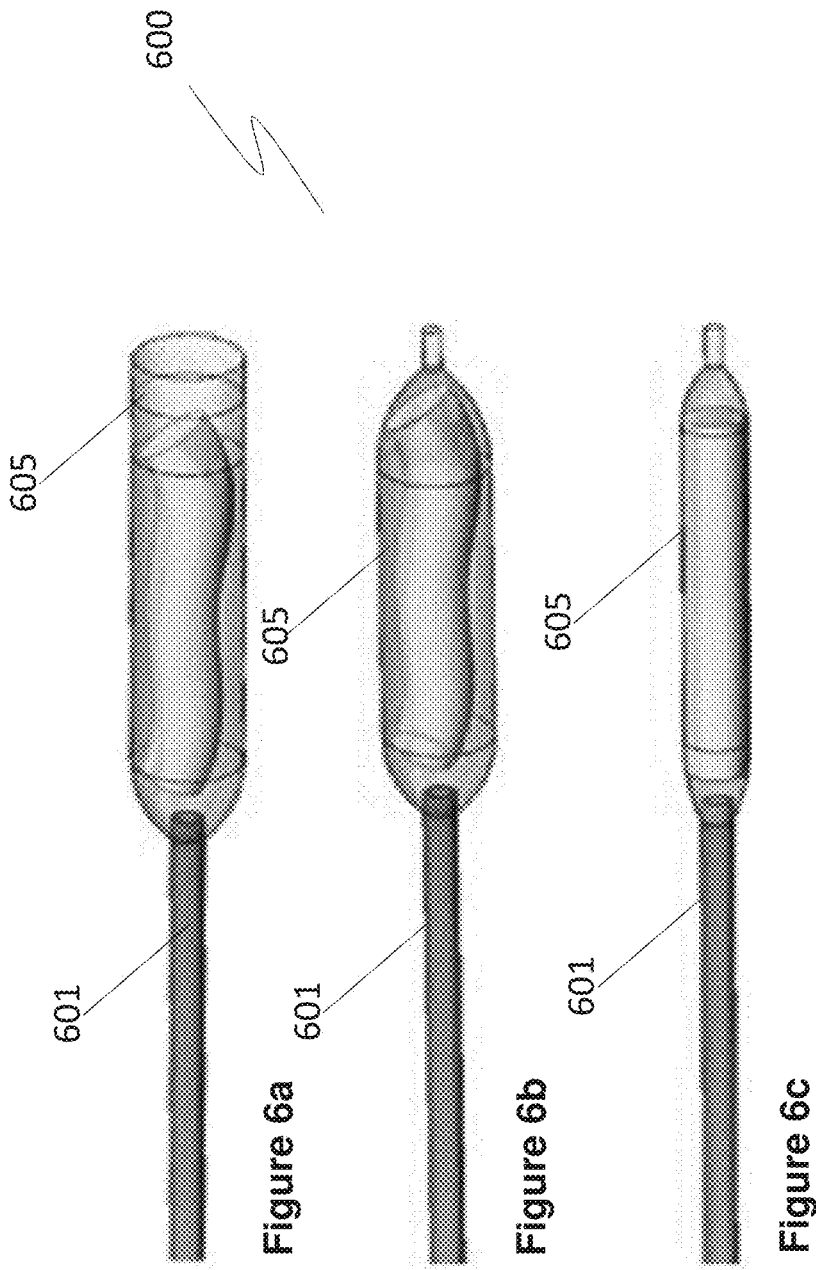
FIGS. 6a to 6c show another embodiment of the device for extraction of tissue from a subject.

FIGS. 6*a* to 6*c* show another embodiment of a device 600 for extraction of tissue from a subject. FIG. 6*a* shows the device 600 in a deployed state surrounding a tissue to be extracted. FIG. 6*b* shows the device 600 having an opening sealed. FIG. 6*c* shows the device 600 arranged in fluid communication with a vacuum device for removal of air within the sealed device before the device 600 is removed from the body cavity.

Device 600 comprises a long flexible rod 601, and a retriever bag 605. In operation, the long flexible rod 601 may be attached to a cylindrical bag 605 with a vacuum seal mechanism. The device 600 can be inserted into the body via the rectum. A long, thin grasper (not shown) may be inserted into the rod 601 by a medical practitioner, which may then emerge at the opening of the bag 605. The medical practitioner (e.g. a surgeon) uses the grasper to grab the end of resected tissue, such as a resected colon and pull it into the bag 605. The bag 605 is then sealed, and vacuum is applied to the end of the rod outside the body. The retrieval bag decreases in volume as air is removed and is pulled out of the body cavity.

To deploy the device 100 of FIG. 1*a*, a user, such as a specialist medical practitioner, may cut or release the elastic band 134 to allow the extractor to be released (but before inflation and extension). As the extractor is pushed through into the body cavity, the anchor portion 108 is inflated/extended and the pliable sleeve is opened up. Once the extractor is inflated and deployed, the introducer 101 may then be pulled out of the body cavity.

To deploy the device 100 depicted in FIG. 1*b*, a user, such as a specialist medical practitioner, may pack the extractor within the cavity 136. The cavity 136 may have an actuator in the form of slidable hollow sleeve 138 that forms a cover over the cavity 136. The hollow sleeve 138 can be moved along an axis of the cavity 136 to expose or cover the extractor.

According to another aspect of the disclosure and with reference to FIG. 7, there is a method 700 of using the device 100, 400, 500 to extract a resected specimen such as a colon tissue from a body cavity of a subject. The method 700 comprises the steps of: a. collapsing and packing the sleeve assembly into a cavity formed on the elongate device (step s702); b. inserting, via the substantially rounded end, the elongate device into a natural canal of the subject (step s704); c. moving the elongate device towards a body cavity where the resected specimen is located (step s706); d. inflating the anchor portion for attachment to a surface of an inner wall of the body cavity of the subject, and extending the pliable sleeve in a manner to define a channel between the first end and second end (step s708); and e. removing the resected colon through the channel (step s710) via the extractor.

Step s708 may further include the following sub-steps.

(i.) After moving the device 100, 400, 500 to the location where the resected specimen is, the anchor portion of the extractor may be released from the introducer via extension or inflation to form a ring.

(ii.) Upon attaching onto the surface of an inner wall of the body cavity, the introducer is then removed from the body.

After removing the resected specimen through the channel via step s710, the anchor portion may then be deflated, or the elastic ring is crimped, and the extractor is pulled out of the body.

In some embodiments (not shown), the introducer may be in the form of a stapling device attached to the extractor in a pre-deployed form. The stapling device may include an elongate portion.

It is contemplated that the device 100, and the method 700 for using the device 100, can include one or more of the following variants and/or combinations:—

(i.) The device 100 may be a surgical device, and/or may preferably be formed of/from biocompatible materials.

(ii.) The legs 132 may be combined with the cavity 136 and the quick-release actuator 138 to form further embodiments.

(iii.) The pliable sleeve 116 may be formed from/of other structures, such as a collapsible stent structure.

(iv.) One or more levers 202 may be combined with one or more spines 210.

(v.) Various parts of the extractor device may be formed from or of elastic or compliant materials, wherein part 108 may be relatively more elastic than the other parts.

In some embodiments, the elongate portion is formed of or from biocompatible materials such as 316L stainless steel and polypropylene.

It should be further appreciated by the person skilled in the art that variations and combinations of features described above, not being alternatives or substitutes, may be combined to form yet further embodiments falling within the intended scope of the invention.

The invention claimed is:

1. A surgical device for extraction of a resected tissue or the like from a body comprising an elongate portion having a substantially rounded end; a sleeve assembly comprising an anchor portion for contacting a region around the resected tissue when inflated or extended to a sufficiently rigid state, and a body portion shaped and dimensioned to receive the resected tissue; the body portion comprises a first end, a second end and a pliable sleeve; the first end and the second end each having a respective diameter greater than a desired diameter of the natural orifice or tissue opening; wherein the pliable sleeve is disposed between the first end and the second end in a manner which a distance between the first end and the second end is adjustable; and a crimping mechanism disposed between the first end and the second end of the pliable sleeve, wherein the crimping mechanism is configured to slide in a longitudinal direction of the pliable sleeve, the crimping mechanism comprising a crimping ring disposed circumferentially around the pliable sleeve, and a support ring disposed along an inner wall of the pliable sleeve, such that the sleeve is sandwiched between the crimping ring and the support ring.

2. The surgical device of claim 1, wherein the elongate portion of the device comprises a cavity adapted to receive the sleeve assembly or part thereof.

3. The surgical device of claim 1, wherein the elongate portion may comprise a first elongate part and a second elongate part, the first elongate part and the second elongate part joined at an angle.

4. The surgical device of claim 1, wherein the elongate portion is formed of or from biocompatible materials.

5. The surgical device of claim 1, wherein the anchor portion is configured to inflate or extended to a sufficiently rigid ring in a body cavity and at a pre-determined temperature.

6. The surgical device of claim 1, wherein the resected tissue is a resected human or animal colon tissue.

7. The surgical device of claim 1, further comprising a spine portion connecting the first end and the second end or positioned between the first end and the second end, the spine portion comprises at least one releasable lever mechanism to move at least one of the first end and the second end between a collapsed state and a non-collapsed state.

8. The surgical device of claim 1, wherein the crimping ring comprises a lever operable to compress the crimping ring, such that longitudinal movement of the locking means, with respect to the first and second ends, is prevented.

9. The surgical device of claim 1, wherein the support ring has a plurality of bumps or other textures disposed along a circumference of the support ring.

10. A method of using the device of claim 1 to extract a resected specimen, comprising the steps of:

a. collapsing and packing the sleeve assembly into a cavity formed on the elongate device;

b. inserting, via the substantially rounded end, the elongate device into a natural canal of a mammalian subject;

c. moving the elongate device towards a body cavity where the resected specimen is located;

d. inflating or extending the anchor portion for attachment to a surface of an inner wall of the body cavity of the mammalian subject, extending the pliable sleeve in a manner to define a channel between the first end and second end;

e. sliding the crimping mechanism along the longitudinal direction of the pliable sleeve prior and clamping the pliable sleeve between the support ring and the crimping ring; and f. removing the resected specimen through the channel.

11. The method of claim 10, wherein the step of removing the resected specimen includes a step of inserting a grasping or crimping device and pulling the resected specimen through the channel.

* * * * *